US010076920B2

(12) United States Patent
Mohmedi

(10) Patent No.: US 10,076,920 B2
(45) Date of Patent: Sep. 18, 2018

(54) CARD WITH INTEGRATED FINGERPRINT AUTHENTICATION

(76) Inventor: Saeid Mohmedi, Aurora (CA)

( * ) Notice: Subject to any disclaimer, the term of this patent is extended or adjusted under 35 U.S.C. 154(b) by 0 days.

(21) Appl. No.: 14/237,236

(22) PCT Filed: Aug. 3, 2012

(86) PCT No.: PCT/CA2012/050533
§ 371 (c)(1),
(2), (4) Date: May 5, 2014

(87) PCT Pub. No.: WO2013/020230
PCT Pub. Date: Feb. 14, 2013

(65) Prior Publication Data
US 2014/0232525 A1 Aug. 21, 2014

Related U.S. Application Data

(60) Provisional application No. 61/515,397, filed on Aug. 5, 2011.

(51) Int. Cl.
*G06K 9/00* (2006.01)
*B42D 25/313* (2014.01)
(Continued)

(52) U.S. Cl.
CPC ........ *B42D 25/313* (2014.10); *A61B 5/02427* (2013.01); *G06K 9/00087* (2013.01);
(Continued)

(58) Field of Classification Search
CPC ......... G06K 9/00087; G06K 19/07354; G06K 9/00; G06K 9/00006; G06K 9/0002;
(Continued)

(56) References Cited

U.S. PATENT DOCUMENTS 5,737,439 A * 4/1998 Lapsley ............... A61B 5/1171
382/115
6,325,285 B1 * 12/2001 Baratelli .............. G06K 7/0021
235/380
(Continued)

FOREIGN PATENT DOCUMENTS

EP     1575004      9/2005
WO     2004025545   3/2004

OTHER PUBLICATIONS

Stensgaard, A.B., "Biometric breakthrough—credit cards secured with fingerprint recognition made feasible", AME info, Apr. 20, 2005 (URL: <http://www.ameinfo.com/pfdocs/58236.pdf>).
(Continued)

*Primary Examiner* — Brian Wilson
(74) *Attorney, Agent, or Firm* — Clayton, McKay & Bailey, PC

(57) ABSTRACT

A card, such as a credit or identification card, including an authenticating element for authenticating the card with a service provider, a fingerprint reader integral with the card for reading a fingerprint provided by a user of the card, and a processing element for comparing the fingerprint provided by the user to a fingerprint of an owner of the card to confirm that the user is the owner. In one variation, there is also provided a means for determining whether an object presented to the fingerprint reader is a finger of the user presenting the card.

4 Claims, 3 Drawing Sheets

(51) Int. Cl.

| | |
|---|---|
| *A61B 5/024* | (2006.01) |
| *G06Q 20/34* | (2012.01) |
| *G06Q 20/40* | (2012.01) |
| *G06K 19/073* | (2006.01) |
| *G07C 9/00* | (2006.01) |
| *G07F 7/08* | (2006.01) |
| *G07F 7/10* | (2006.01) |
| *B42D 25/00* | (2014.01) |

(52) U.S. Cl.
CPC ..... *G06K 19/07354* (2013.01); *G06Q 20/341* (2013.01); *G06Q 20/40145* (2013.01); *G07C 9/00087* (2013.01); *G07F 7/0826* (2013.01); *G07F 7/0833* (2013.01); *B42D 25/00* (2014.10); *G07C 2009/00095* (2013.01); *G07F 7/1008* (2013.01)

(58) Field of Classification Search
CPC ........... G06K 9/00107; G06K 9/00114; G06K 9/0012; G06K 9/00127; G06K 19/0718; G07F 7/0826; G07F 7/0833; G07F 7/1008; G07F 7/08; G07F 7/0806; G07F 7/0813; G07F 7/082; G07F 7/10; G06Q 20/341; G06Q 20/40145; G06Q 20/34; G06Q 20/354; G06Q 20/40; G06Q 20/401; G07C 2009/00095; G07C 9/00087; B42D 25/00; B42D 25/30; B42D 25/313
See application file for complete search history.

(56) References Cited

U.S. PATENT DOCUMENTS

| | | | | |
|---|---|---|---|---|
| 6,483,929 | B1* | 11/2002 | Murakami | G06K 9/00496 340/5.83 |
| 6,643,531 | B1* | 11/2003 | Katarow | A61B 5/1172 600/323 |
| 2003/0141959 | A1* | 7/2003 | Keogh | G07C 9/00563 340/5.53 |
| 2004/0129787 | A1* | 7/2004 | Saito | G06K 19/07 235/492 |
| 2004/0133787 | A1 | 7/2004 | Doughty et al. | |
| 2005/0030724 | A1* | 2/2005 | Ryhanen | A61B 5/117 361/760 |
| 2005/0053264 | A1* | 3/2005 | Amano | G06K 9/0002 382/115 |
| 2005/0194452 | A1 | 9/2005 | Nordentoft et al. | |
| 2005/0240778 | A1 | 10/2005 | Saito | |
| 2008/0253625 | A1 | 10/2008 | Schuckers et al. | |
| 2010/0113952 | A1 | 5/2010 | Raguin et al. | |
| 2011/0170750 | A1 | 7/2011 | Kropp et al. | |
| 2012/0298757 | A1* | 11/2012 | Kim | G06K 19/0718 235/487 |

OTHER PUBLICATIONS

Pishva, D., "Use of spectral biometrics for aliveness detection", Advanced biometric technologies, pp. 133-154, publication.

* cited by examiner

CARD WITH INTEGRATED FINGERPRINT AUTHENTICATION

RELATED APPLICATIONS

This application claims priority to U.S. Provisional Application No. 61/515,397 filed Aug. 5, 2011, the contents of which are herein expressly incorporated by reference.

FIELD OF THE INVENTION

The invention relates generally to authentication systems, and more particularly to a card, such as a payment or identification card, having integrated fingerprint authentication.

BACKGROUND OF THE INVENTION

The need for multi-factor authentication in electronic transactions and other access control systems is increasing. Identity theft, and other threats increase with growing use of e-commerce and e-government solutions. Examples of existing multi-factor authentication solutions include requiring a user name-password pair, or the presence of a device such as a credit card and the knowledge of a PIN. One problem associated with these existing solutions is that they do not guarantee the presence of the owner of the card. Other manual-type arrangements include merchants requesting identification, such as a driver's license, to confirm the identity of the person using the card. Traditional access control schemes use names and passwords. Such systems are vulnerable to many known attacks such as replay and brute force attacks, as is well known.

The financial services industry has been deploying magnetic strip cards for many years. Magnetic strip cards together with a PIN build a two factor authentication system but can be cloned at a fairly low cost. The PIN can be obtained by deploying terminals or point of sales devices that have been tampered with to record the entered PIN. Instances of such abuse have been widely reported in the media.

Recently magnetic strip cards have begun to be phased out by major banks and credit card companies who have started the migration from magnetic stripe cards to chip and pin cards. Chip and pin cards provide a higher level of security because the knowledge of the credit card number, and other exposed credentials of the account and card holder is not sufficient to complete a transaction. The presence of the payment device such as a credit card equipped with a smart card chip is required.

Smart cards are tamper resistant computing devices that provide a secure environment for storing credentials and processing sensitive information. Traditionally, operating a smart card requires the knowledge of a 4 digit pin. Presenting a wrong pin to a smart card repeatedly causes the card to enter the "locked" state and to refuse to communicate with a terminal or card reader. In any event, the card can still be stolen, and used with knowledge of the associated pin. Using a pin has several disadvantages, including (1) a pin can be lost or forgotten, (2) the pin can be obtained from the card owner by force or theft, (3) a pin requires a keypad on the terminal, (4) it takes time to enter, and (5) is not practical if contact-less smart cards are used, because the time in which the card is in the vicinity of the reader may not be sufficient.

A common problem with all these prior art methods is that they do not ensure the presence of the user. Accordingly, there is a need in the art for improved authentication of card-based systems, such as card-based payment systems or card-based personal identification systems.

SUMMARY OF THE INVENTION

It is an object of the invention to solve one or more of the above identified problems with the prior art. Accordingly, there is provided in one embodiment of the invention, a card including an authenticating element for authenticating the card with a service provider, a fingerprint reader integral with the card for reading a fingerprint provided by a user of the card, and a processing element for comparing the fingerprint provided by the user to a fingerprint of an owner of the card to confirm that the user is the owner.

According to one aspect of this embodiment, the fingerprint reader comprises an array of conductive elements that form capacitors when in contact with skin of the user to generate an array of capacitances.

According to another aspect of this embodiment, the processing element generates a model of the fingerprint provided by the user based on the array of capacitances to compare with one of a model and an array of capacitances stored for the fingerprint of the owner.

According to another aspect of this embodiment, the processing element is adapted to prevent the authenticating element from authenticating the card with the service provider if the fingerprint provided by the user does not match the fingerprint of the owner.

According to another aspect of this embodiment, the authenticating element comprises a contact element selected from group consisting of a chip and a bar code.

According to another aspect of this embodiment, the authenticating element comprises a chip, and wherein the chip is adapted to receive power from a terminal into which the card is inserted; the chip in communication with the processing element to provide power to one or more of the processing element and the fingerprint reader.

According to another aspect of this embodiment, the processing element is adapted to receive energy via electromagnetic induction from a contactless terminal with which the authenticating element communicates.

According to another aspect of this embodiment, the processing element is further adapted to provide power to the fingerprint reader.

According to another aspect of this embodiment, there is further provided a means for determining whether the fingerprint provided by the user is a fingerprint of the user.

According to another aspect of this embodiment, the means for determining comprises a photoplethysmogram device.

According to another aspect of this embodiment, the photoplethysmogram device includes a light emitting diode for illuminating skin of the user and a photo diode for measuring changes in light absorption; wherein the illuminating and the measuring changes in light absorption provides an indication of blood flow in a finger of the user.

According to another aspect of this embodiment, the processing element is adapted to provide power to the light emitting diode and to the photo diode upon detection of the fingerprint provided by the user in the fingerprint reader.

According to another aspect of this embodiment, the processing element further compares the changes in light absorption with predetermined reference values indicative of cardiovascular activity in the finger.

According to another embodiment of the invention, there is provided a fingerprint reading device including a fingerprint reader integral with the fingerprint reading device for reading a fingerprint provided by a user, a processing element for comparing the fingerprint provided by the user to a fingerprint of an owner of the fingerprint reading device to confirm that the user is the owner, and a means for determining whether the fingerprint provided by the user is a fingerprint of the user.

According to one aspect of this second embodiment, the means for determining is a photoplethysmogram device.

According to another aspect of this embodiment, the photoplethysmogram device includes a light emitting diode for illuminating skin of the user and a photo diode for measuring changes in light absorption; wherein the illuminating and the measuring changes in light absorption provides an indication of blood flow in a finger of the user.

According to another aspect of this embodiment, the processing element is adapted to provide power to the light emitting diode and to the photo diode upon detection of the fingerprint provided by the user in the fingerprint reader.

According to another aspect of this embodiment, the processing element further compares the changes in light absorption with predetermined reference values indicative of cardiovascular activity in the finger.

DETAILED DESCRIPTION

The various embodiments of the invention described herein below generally include a fingerprint sensor and analyzer embedded within a card, and various other elements that enable different functionality and features of the invention as described. While the invention is generally described with respect to a payment card, such as one having a chip and requiring a user-entered pin, the invention is not limited to such cards. For example, identification cards such as a driver's license may use the invention as herein described, as may health cards, social security cards and various other types of government issued identification cards. Other types of payment processing cards are contemplated as well, such as contact-less cards. While each of these cards, and other prior art systems, are capable of authenticating the card with respect to a service provider, a merchant, a governmental organization or a payment processing service (hereinafter referred to generally as, "the service provider"), the invention is particularly useful in authenticating the card with respect to the owner of the card and may be altogether independent of the service provider or any other entity with which the card is authenticated other than the owner. Of course, in some embodiments the authentication used may also be used to authenticate for the purposes of the service provider.

Figure 1:
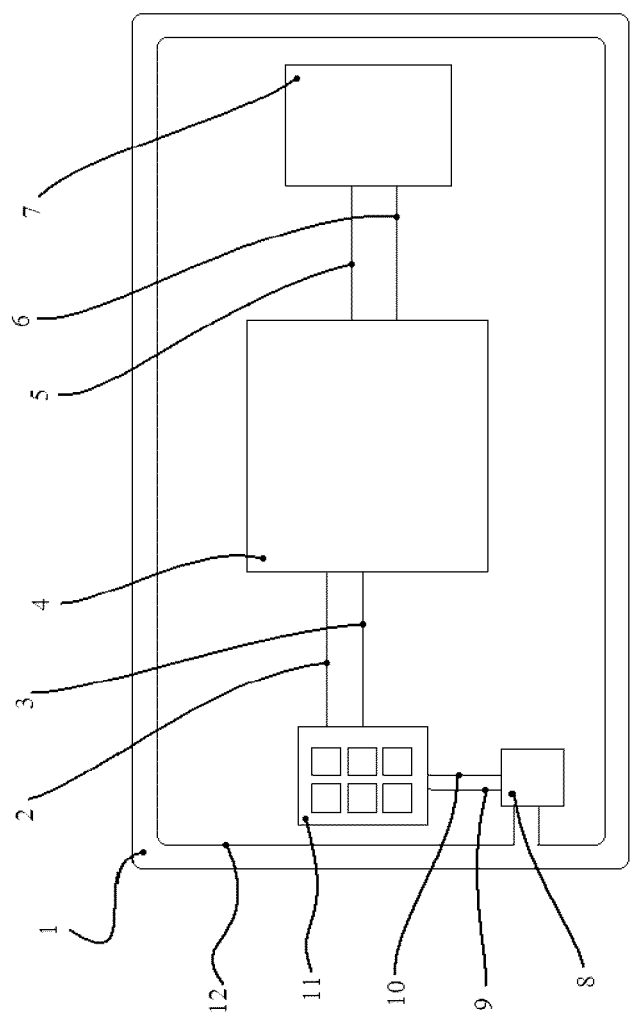
FIG. 1 is a schematic view of a card according to one embodiment of the invention.

Referring now to FIG. 1, there is shown one embodiment of the invention in which a card 1 is provided having a fingerprint reader 7 attached to a surface, or otherwise embedded in the body of the card 1. The card 1 may be any type of card used to identify or authenticate a person, service or account. Non-limiting examples include a credit card, a bank card, a driver's license, and a social security card. In the illustrated embodiment, the card 1 includes an authenticating element in the form of a chip 11 for authenticating the card with a service provider. For example, the chip 11 may be used in combination with a pin to authenticate a credit card with a payment processor or a bank card with an associated bank account. The chip 11 also provides an interface with which the card 1 communicates with a terminal into which the card is inserted during use, as is known in typical chip and pin card arrangements. Interfaces with the terminal being used are generally know in the art and accordingly are not described in further detail.

The fingerprint reader 7 may be any sensor or known fingerprint reader that can capture data representative of a fingerprint presented to the reader. Various fingerprint readers and sensors are known in the art, and may be used or otherwise adapted for implementation onto the card 1. For example, a fingerprint sensor in the form of a two dimensional array of conductive elements may be provided that has a thickness sufficiently thin to be provided on the card 1. Once a finger touches the array of conductive elements, the elements together with the changes in elevation on the fingerprint results in an array of capacitors with different capacitances. This information can be processed into a model or data representative of a fingerprint for comparison with a known model or known data of a predefined fingerprint, which is typically a known fingerprint of the owner of the card.

The data gleaned from the fingerprint reader or sensor 7 is preferably processed by processing element 4 to determine whether a fingerprint provided by the user matches the known fingerprint of an owner of the card. The known fingerprint may be stored on a memory element on the card with which the processing element is in communication. The processing element 4 may include a central processing unit forming part of a computing device arranged in the circuitry as illustrated in FIG. 1. The processing element 4 may alternatively be a micro controller or a smart card chip capable of carrying out the processing, and in some embodiments, is formed integrally with the chip 11.

Stored on memory in communication with the processing element 4 is an algorithm that can be used to generate the data or model of the presented fingerprint based on the capacitances measured as described above. A further algorithm may be provided to compare the sensed fingerprint with one of the owner stored in memory. The fingerprint reader 7, processing element 4, memory and the chip 11 may in communication via a number of on-card wires or conductive materials formed integral with the card. These paths are illustrated generally as connections 2, 3, 5, and 6 in FIG. 1. The conductive wires 5 preferably provide the fingerprint reader 7 with power, and are transmitted thereto by the processing element 4, which receives power from the contact interface of chip 11 when it is inserted into a receiving terminal (not shown). The contact interface 11 is the electrical interface between the card, including the elements thereon, and the card reader or terminal. One or more conductive paths 2, 3 connect the interface 11 to the processing element 4 and are used to transfer information between the interface 11 and the processing element 4. The interface 11 may be a typical chip known in the prior art.

When a card user holds the card 1 and inserts it into a terminal, for example a terminal at a retailer, a finger (typically the thumb) is required to be placed on the fingerprint reader 7. The contact interface 11 connects to a corresponding connector within the terminal where it receives and transmits electrical power to the processing element 4 and to the fingerprint reader 7. The finger placed on the fingerprint reader is then captured by the reader 7 and communicated to the processing element 4, which uses an algorithm to convert the data received from the reader 7 into a form that can be compared with a previously stored fingerprint. The previously stored fingerprint would be that of the owner of the card. Upon comparing the presented fingerprint to the stored fingerprint, the processing element 5 prevents the authenticating element from authenticating the card with a service provider, or in an alternate embodiment, prevents the card from communicating with the terminal, thus aborting a transaction. Other protocols of action based on when the fingerprints do not match are also contemplated by the invention, such as disabling the card or placing a report to law enforcement authorities regarding the false use of a particular card.

In an alternate embodiment, the card 1 can be used in contactless operation in which an antenna and a modulator or radio 9 are used instead of the contact interface 11. These types of cards are increasing in popularity, particularly for smaller transactions. In this embodiment, the terminal is adapted to receive power via electromagnetic induction, and transfers power to the fingerprint reader and processing element in a manner similar to that described above. Information is communicated between the card and the terminal via the modulator or radio 9 and the antenna on the terminal. The user will have to maintain the card in close proximity to the terminal to provide sufficient time for power to be provided to the fingerprint reader and processing to occur by the processing element.

In some embodiments, the card can also be provisioned by the certificate of a certification authority such as a government agency or other organization. The card generates a key pair such as an RSA or ECC key pair. The private key is never exposed to any entity. The card may also be provisioned with a set of symmetric keys. These keys may be used for session key derivation or other cryptographic operation while the card is in use.

The card generates a certificate request and submits its public key to the certification authority. This request may contain name or other information about the card holder. The fingerprint of the card-holder is captured using the card and stored in the card. The fingerprint may be signed and/or encrypted using the cards keys and then stored.

In other embodiments of use, card holder places his finger/thumb on the scanner and presents the card to a terminal. The terminal provides power to the card. The card and the terminal may perform mutual authentication using keys and/or certificates mentioned above to establish trust. This may be done using a challenge-response procedure. The terminal issues commands to the card to scan the user's fingerprint and verify it against the stored fingerprint. The terminal receives a signal from the card indicating whether the said verification was successful together with the name and other relevant information of the card holder. This information may be signed using the private key of the card. The terminal can trust the identification information obtained from the card based on the keys and certificates issued at the time of provisioning. In addition this system ensures the presence of the legitimate card-holder at the terminal at the time of transaction. In the above scenario, the fingerprint of the card holder never leaves the card and is not stored in any external storage. This feature provides a higher level of security and protects the card holder. On the other hand the cost of storing, transporting, and managing a large number of biometric information in a central database is saved.

The aforementioned card may further be augmented by providing an additional mechanism against extreme fraud, whereby a means is provided for determining whether the fingerprint being read by the fingerprint reader is provided by a live person. This may be particularly useful in embodiments where the card is an identification card or security card for uses where enhanced security is required. It is conceivable that "false" fingers may be created to mimic the fingerprint of a user in an attempt to circumvent the fingerprint authentication of the card. In order to address this possibility, applicant has developed the use of photoplethysmogram (PPG) implemented on the card 1, to detect cardiovascular activity in the finger being presented to ensure that a live user is present.

Figure 2:
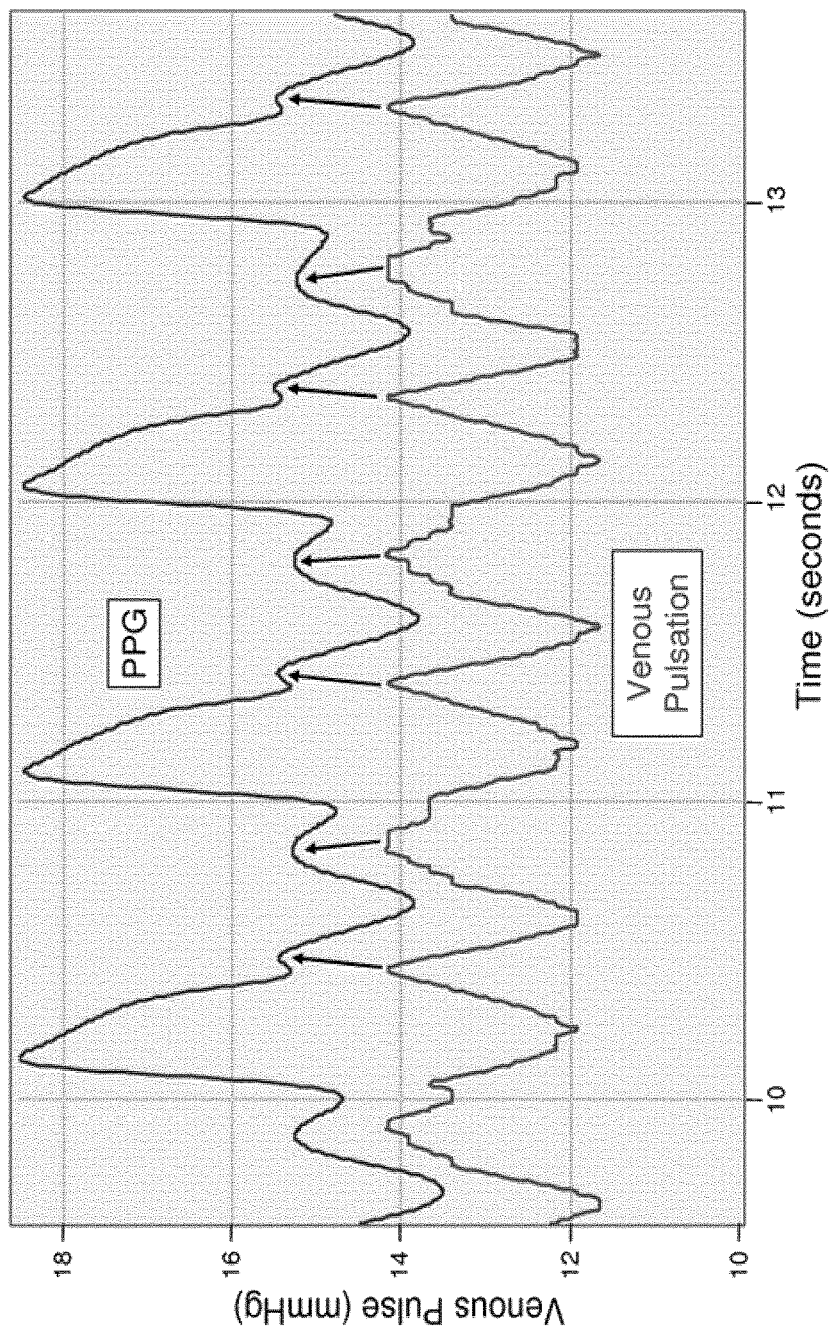
FIG. 2 is a graph showing representative PPG readings according to a second embodiment of the invention.

PPG's provide a volumetric measurement of an organ and are often obtained using a pulse oximeter which illuminates the skin and measures changes in light absorption. A conventional pulse oximeter monitors the perfusion of blood to the dermis and subcutaneous skin tissue, but is typically too large to be implemented on a card as herein described. With each cardiac cycle, the heart pumps blood to the periphery. The change in volume caused by the pressure pulse is detected by illuminating the skin and then measuring the amount of light either transmitted or reflected. Each cardiac cycle appears as a peak, for example as shown in FIG. 2.

Figure 3:
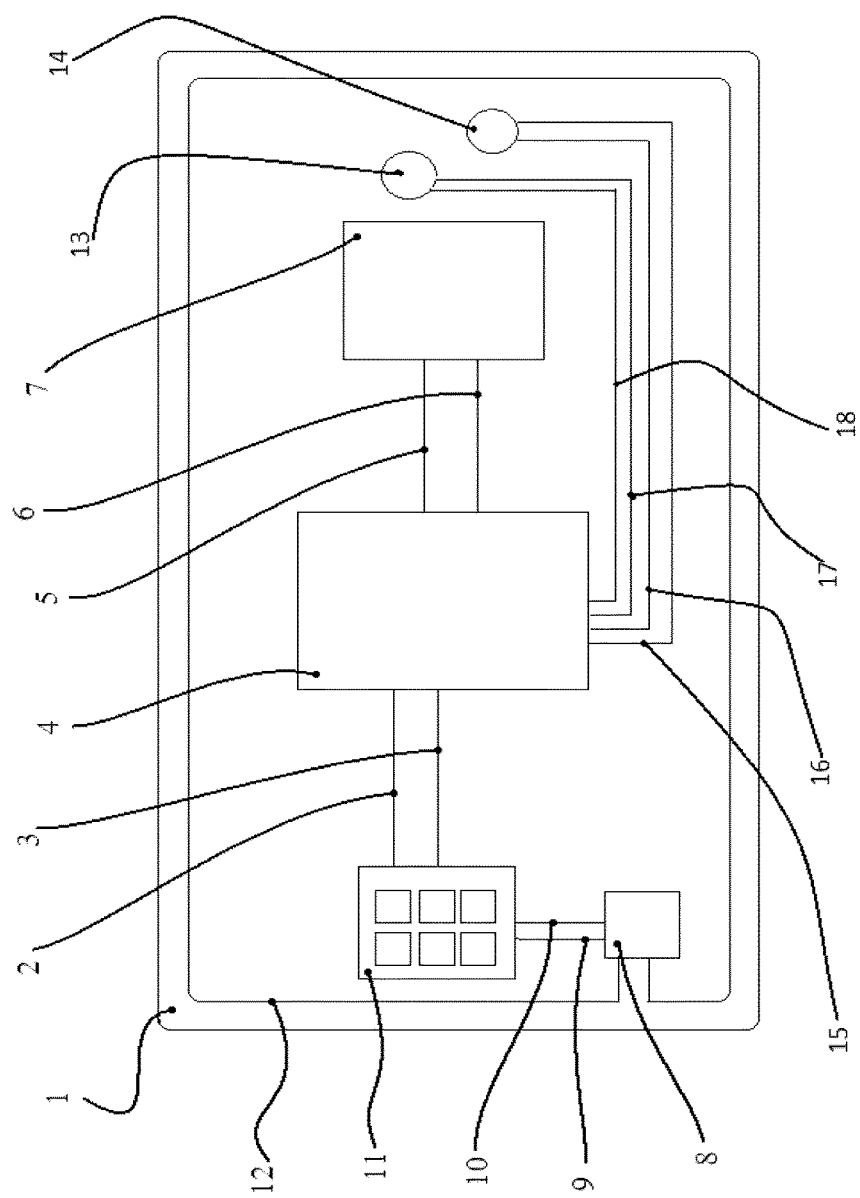
FIG. 3 is a schematic view of a card according to the second embodiment of the invention.

Referring now to FIG. 3, applicant provides a modified PPG for implementation on a card according to the invention to determine whether the finger being presented to the fingerprint reader is indeed a live finger of the user presenting the fingerprint. Accordingly, model fingers will be rejected, as described below, as will amputated fingers or surfaces onto which a fingerprint may otherwise be replicated. In FIG. 3, like elements from FIG. 1 are numbered in a corresponding manner, and accordingly are not described in further detail. The embodiment of FIG. 3 further includes a light-emitting element, preferably light-emitting diode 13 and a photo element, preferably photo diode 14, in communication with the processing element 4 via conductive elements 15, 16, 17 and 18. 10. Each of the light-emitting 13 and photo 14 diodes are powered and controlled by the processing element in a manner analogous to how the fingerprint reader/sensor 7 is powered and controlled. The photo diode element 14 is preferably placed in close proximity with the light-emitting diode element 13 and is located at a position on the card whereby when an object (typically the finger of a user) is placed on the fingerprint reader 7, the object also covers the light-emitting 13 and photo 14 diodes. The processing element 4, is adapted to receive and process signals from the photo diode 14 after the object has been illuminated by the light-emitting diode 13. The photo diode 14 captures data indicative of the amount of light reflected to the photo diode 14 from the illuminated object. The change in volume caused by pressure pulses in the thumb results in the data that has been shown in FIG. 2. For the purposes of this invention, it is not particularly relevant how accurate the measurements or processing carried out by the processing element 14 are, in that any given threshold change in volume that is detected in a pulsating manner is sufficient to indicate that the object in the fingerprint reader is a finger of a live person. Pulses of the magnitude indicated in FIG. 2 are representative of being sufficient for identifying cardiovascular activity in the finger being read.

Preferably, the processing element 14 compares the signals received from the photo-diode 14 with reference values stored in memory and if the comparison yields results indicative of the object in the fingerprint reader being that of a finger of the user, then the fingerprint is read by the fingerprint reader and the processing element 14 permits communication by the card with a terminal as was described with respect to the first embodiment, on condition that the fingerprint being presented is confirmed to be that of the owner of the card. Alternatively, if the processing element 11 determines that the object being presented is not the finger of a user of the card, then communication between the chip 11 and the terminal is prevented. Optionally, this cessation of operation can be carried out by preventing a fingerprint from being read by the sensor 7 if the presented object is deemed not to be that of the finger of the user, which would also prevent communication with the terminal as no fingerprint match will be achieved.

This second embodiment of the invention is also applicable to fingerprint readers generally, and particularly to portable fingerprint readers. That is, a condition of reading a fingerprint by a sensor may be made dependent upon confirmation from a processing element that data received from the photo diode after illumination by a light-emitting diode is indicative of cardiovascular activity such that it can be confirmed that an object being presented to the fingerprint reader is indeed the finger of a live and present user. In this variation, the processing element prevents the fingerprint sensor from reading a fingerprint if the object is deemed not to be the finger of a live and present user. Without a fingerprint being read, the fingerprint reader will not function and no comparison will be made to match the read fingerprint to a reference fingerprint stored in memory.

Various modifications to the invention are contemplated without departing from the spirit and scope of the invention which is defined in the claims that follow. While various steps and computer components have been herein used, these are to be given their ordinary definition as would be known in the art, unless explicitly limited or otherwise herein defined. The above-described embodiments are intended to be examples of the present invention and alterations and modifications may be effected thereto, by those of skill in the art, without departing from the scope of the invention that is defined solely by the claims appended hereto.

We claim:

1. A card comprising:
    an authentication element for authenticating the card with a service provider via a terminal, the card having a front surface;
    a photoplethysmogram device for determining whether a fingerprint provided by a finger of a user is from a live person, the photoplethysmogram device including a light emitting diode for illuminating the skin of the user and a photo diode for measuring changes in light absorption in the finger of the user;
    a fingerprint reader integral with the card for reading the fingerprint of the user;
    the fingerprint reader including an array of conductive elements that form capacitors when in contact with the finger of the user to generate an array of capacitances;
    a processing element for comparing the changes in light absorption with predetermined reference values stored on the card indicative of cardiovascular activity in a finger and for comparing the fingerprint of the user to a fingerprint of an owner of the card to confirm the user is the owner,
    wherein the processing element is configured to activate the fingerprint reader to read the fingerprint of the user after confirming, based on the comparison of the changes in light absorption with the predetermined reference values, cardiovascular activity in the finger of the user; and
    wherein the photo diode, the light emitting diode, and the fingerprint reader are co-planar with the front surface of the card.

2. The card according to claim 1, wherein upon a condition in which the fingerprint of the user is not confirmed as the fingerprint of the owner of the card, preventing communication between the card and the terminal.

3. The card according to claim 1, wherein the terminal provides power to the card.

4. A system comprising a terminal providing power to a card, wherein the terminal issues commands to the card to scan a fingerprint of a finger of a user and compare it against a fingerprint of an owner stored in memory on the card; and wherein the terminal receives a signal from the card confirming whether the comparison was successful together with identification information of the owner; said identification information being signed using a private key of the card,
    the card comprising:
        a photoplethysmogram device for determining whether the fingerprint provided by the user is from a live person, the photoplethysmogram device including a light emitting diode for illuminating the skin of the user and a photo diode for measuring changes in light absorption in the finger of the user;
        a fingerprint reader integral with the card for reading the fingerprint of the user; the fingerprint reader including an array of conductive elements that form capacitors when in contact with the finger of the user to generate an array of capacitances;
        a processing element for comparing the changes in light absorption with predetermined reference values stored on the card indicative of cardiovascular activity in a finger and for and comparing the fingerprint of the user to the fingerprint of the owner of the card to confirm the user is the owner;
        wherein the processing element is configured to activate the fingerprint reader to read the fingerprint of the user after confirming, based on the comparison of the changes in light absorption with the predetermined reference values, cardiovascular activity in the finger of the user; and
        wherein the photo diode, the light emitting diode, and the fingerprint reader are co-planar with a front surface of the card.

\* \* \* \* \*